US005637573A

United States Patent [19]
Agrawal et al.

[11] Patent Number: 5,637,573
[45] Date of Patent: Jun. 10, 1997

[54] INFLUENZA VIRUS REPLICATION INHIBITING OLIGONUCLEOTIDE ANALOGUES AND THEIR PHARMACEUTICAL COMPOSITIONS

[76] Inventors: Sudhir Agrawal, 46G Brandywine Dr., Shrewsbury, Mass. 01545; Josef M. E. Leiter, 111 Hicks St., #25C, Brooklyn, N.Y. 11201; Peter Palese, 414 Highwood Ave., Leonia, N.J. 07605; Paul C. Zamecnik, 29 LeBeaux Dr., Shrewsbury, Mass. 01545

[21] Appl. No.: 483,497

[22] Filed: Jun. 7, 1995

Related U.S. Application Data

[63] Continuation of Ser. No. 960,122, Oct. 13, 1992, abandoned, which is a continuation of Ser. No. 516,275, Apr. 30, 1990, Pat. No. 5,194,428, which is a continuation-in-part of Ser. No. 160,574, Feb. 26, 1988, abandoned, which is a continuation-in-part of Ser. No. 71,894, Jul. 10, 1987, abandoned, which is a continuation-in-part of Ser. No. 867,231, May 23, 1986, Pat. No. 4,806,463.

[51] Int. Cl.$^6$ ............................. A61K 31/70; C07H 21/00
[52] U.S. Cl. ............................. 514/44; 536/23.1; 536/24.5
[58] Field of Search ............................. 536/24.5, 23.1; 514/44

[56] References Cited

U.S. PATENT DOCUMENTS

| | | | |
|---|---|---|---|
| 4,469,863 | 9/1984 | Ts'o et al. | 536/25.4 |
| 4,511,713 | 4/1985 | Miller et al. | 514/44 |
| 4,587,044 | 5/1986 | Miller et al. | 530/211 |
| 4,689,320 | 8/1987 | Kaji | 514/44 |
| 4,806,463 | 2/1989 | Goodchild et al. | 435/5 |
| 5,194,428 | 3/1993 | Agrawal et al. | 514/44 |

FOREIGN PATENT DOCUMENTS

| | | |
|---|---|---|
| 0169787 | 1/1986 | European Pat. Off. |
| 0288163 | 10/1988 | European Pat. Off. |
| 0300687 | 1/1989 | European Pat. Off. |
| 8301451 | 4/1983 | WIPO |
| 8605516 | 9/1986 | WIPO |
| 8703451 | 6/1987 | WIPO |

OTHER PUBLICATIONS

Kawaoka et al., "Avian-to-Human Transmission of the PB1 Gene of Influenza A Viruses in the 1957 and 1968 Pandemics," *J. Virology*, 63, 4603–4608 (1989).

Winter et al., "Nucleotide Sequence of Human Influenza A/PR/8/34 Segment 2," *Nucleic Acids Research*, 10, 2135–2143 (1982).

Cox et al., "Identification of Sequence Changes in the Cold–Adapted, Live, Attenuated Influenza Vaccine Strain, A/Ann Arbor/6/60 (H2N2)," *Virology*, 167, 554–567 (1989).

Nayak et al., "Complete Sequence Analysis Show that Two Defective Interfering Influenza Viral RNAs Contain a Single Internal Deletion of a Polymerase Gene," *Proc. Nat. Acad. Sci. USA*, 79, 2216–2220 (1982).

Jennings et al., "Does the Higher Order Structure of the Influenza Virus Ribonucleoprotein Guide Sequence Rearrangements in Influenza Viral RNA?" *Cell*, 34, 619–627 (1983).

Yamashita et al., "Comparison of the Three Large Polymerase Proteins of INfluenza A, B, and C Viruses," *Virology*, 171, 458–466 (1989).

Marcus–Sekura et al., "Comparative Inhibition of Chloramphenicol Acetyl Transferase Gene Expression by Antisense Oligonucleotide Analogues Having Alkyl Phosphotriester, Methylphosphonate and Phosphorothioate Linkages," *Nucleic Acids Research*, 15(14), 5749–5763 (1987).

Zon, "Oligonucleotide Analogues as Potential Chemotherapeutic Agents (Review)," *Pharamceutical Res.*, 5(9), 539–549 (1988).

Goodchild, "Conjugates of Oligonucleotides and Modified Oligonucleotides: A Review of Their Synthesis and Properties," *Bioconjugate Chem.*, 1(3), 165–186 (1990).

Stridh et al., "Functional Analysis of Influenza RNA Polymerase Activity by the Use of Caps, Oligonucleotides and Polynucleotides," *Antiviral Res.*, 1, 97–105 (1981).

Romans et al., "Identification of the Influenza Virus Transcriptase by Affinity–Labeling with Pyridoxal 5'–Phosphate," *Virology*, 132, 110–117 (1984).

Stephenson et al., "Inhibition of Rous Sarcoma Viral RNA Translation by a Specific Oligodeoxyribonucleotide," *Proc. Natl. Acad. Sci. USA*, 75(1), 285–289 (1978).

Torrence et al., "Strategies in the Design of Oligonucleotides as Potential Antiviral Agents," published in *Targets for the Design of Antivirals*, DeClercq & Walker (eds.), Plenum Press, vol. 73, NATO ASI Series, 1984, New York, NY, pp. 259–285.

Miller et al., "Nonionic Oligonucleotide Analogs as New Tools for Studies on the Structure and Function of Nucleic Acids Inside Living Cells," published in *Nucleic Acids: The Vectors of Life*, D. Reidel Publishing Co., 1983, pp. 521–535.

Zamecnik et al., "Inhibition of Rous Sarcoma Virus Replication and Cell Transformation by a Specific Oligodeoxynucleotide," *Proc. Natl. Acad. Sci. USA*, 75(1), 280–284 (1978).

Van derKrol et al., *Biotechniques*, 6(10), 958–976 (1988).

Helene et al., *Genome*, 31(1), 413–421 (1989).

(List continued on next page.)

*Primary Examiner*—John Kight
*Assistant Examiner*—L. Eric Crane

[57] ABSTRACT

A method of inhibiting influenza virus replication through the activity of natural (unmodified) or modified oligonucleotides (oligodeoxynucleotides or oligoribonucleotides) which hybridize to a selected region of the influenza virus RNA and interfere with its ability to serve as a template for synthesis of encoded products. Oligonucleotides (unmodified or modified) which have antiviral activity against influenza virus as a result of their ability to hybridze to a selected region of influenza virus RNA and inhibit its ability to serve as a template for synthesis of encoded products, as well as compositions which include the oligonucleotides.

5 Claims, 7 Drawing Sheets

OTHER PUBLICATIONS

Toulme et al., *Gene,* 72, 51–58 (1988).
Ts'o et al., *Ann. New York Acad. Sci.,* 507, 220–241 (1987).
Stridh et al., *Antiviral Research,* 1, 97–105 (1981).
Vlassov et al., *Adv. in Enzyme Regulation,* 24, 301–322 (1985).
Zerial et al., *Nucleic Acids Res.,* 15(23), 9909–9919 (1987).
Agris et al., *Biochemistry,* 25(20), 6268–6275 (1986).
Lemaitre et al., *Proc. Nat. Acad. Sci. USA,* 84, 648–652 (1987).
Kabanov et al., *FEBS Letters,* 259, 327–330 (1990).
Harper et al., *Proc. Nat. Acad. Sci. USA,* 83, 772–776 (1986).
Smith et al., *Proc. Nat. Acad. Sci. USA,* 83(9), 2787–2791 (1986).
Zamecnik et al., *Proc. Nat. Acad. Sci. USA,* 83, 4143–4146 (1986).
Zon et al., "Phosphorothioate Oligonucleotides," Ch. 4 in *Oligonucleotides and Analogues: A Practical Approach,* IRL Press, New York, NY, 1991, pp. 87–108.

INFLUENZA VIRUS REPLICATION INHIBITING OLIGONUCLEOTIDE ANALOGUES AND THEIR PHARMACEUTICAL COMPOSITIONS

RELATED APPLICATIONS

The application is a continuation of U.S. Ser. No. 07/960,122, filed Oct. 13, 1992, now abandoned, which is a continuation of U.S. Ser. No. 07/516,275, filed Apr. 30, 1990, now U.S. Pat. No. 5,194,428, which is a continuation-in-part of U.S. Ser. No. 07/160,574 filed Feb. 26, 1988, now abandoned, which is a continuation-in-part of U.S. Ser. No. 07/071,894, filed Jul. 10, 1987, now abandoned, which is a continuation-in-part of U.S. Ser. No. 06/867,231, filed May 23, 1986, now U.S. Pat. No. 4,806,463. The teachings of these three related applications are incorporated herein by reference.

FUNDING

Work described herein was supported by the National Institutes of Health, the Boehringer Ingelheim Foundation, the G. Harold and Leila Y. Mathers Foundation, the Worcester Foundation for Experimental Biology and the Mount Sinai School of Medicine.

BACKGROUND

Influenza A virus is a membrane-enclosed virus whose genome is a segmented minus strand of RNA. The ten influenza virus genes are present on eight segments of the single-stranded RNA of strains A and B, and on seven segments of strain C. The segments are of varying sizes (ranging from 890 to 2341 nucleotides in length) and each is a template for synthesis of different mRNA. The influenza virus virion contains virus-specific RNA polymerases necessary for mRNA synthesis from these templates and, in the absence of such specific polymerases, the minus strand of influenza virus RNA is not infectious. Initiation of transcription of the mRNAs occurs when the influenza virus mRNA polymerase takes 12 to 15 nucleotides from the 5' end of a cellular mRNA or mRNA precursor and uses the borrowed oligonucleotide as a primer. Generally, the mRNAs made through this process encode only one protein. The M RNA and the NS RNA also code for spliced mRNAs, which results in production of two different proteins for each of these two segments.

Influenza viruses infect humans and animals (e.g., pigs, birds, horses) and may cause acute respiratory disease. There have been numerous attempts to produce vaccines effective against influenza virus. None, however, have been completely successful, particularly on a long-term basis. This may be due, at least in part, to the segmented characteristic of the influenza virus genome, which makes it possible, through reassortment of the segments, for numerous forms to exist. For example, it has been suggested that there could be an interchange of RNA segments between animal and human influenza viruses, which would result in the introduction of new antigenic subtypes into both populations. Thus, a long-term vaccination approach has failed, due to the emergence of new subtypes (antigenic "shift"). In addition, the surface proteins of the virus, hemagglutinin and neuraminidase, constantly undergo minor antigenic changes (antigenic "drift"). This high degree of variation explains why specific immunity developed against a particular influenza virus does not establish protection against new variants. Hence, alternative antiviral strategies are needed. Although influenza B and C viruses cause less clinical disease than the A types, chemical antivirals should also be helpful in curbing infections caused by these agents.

SUMMARY OF THE INVENTION

The present invention relates to a method of inhibiting (reducing or preventing) influenza virus replication through the activity of natural (unmodified) or modified oligonucleotides (i.e., oligodeoxynucleotides or oligoribonucleotides which hybridize to a selected region of the influenza virus RNA and interfere with (reduce or eliminate) its ability to serve as a template for synthesis of encoded products (e.g., RNA, DNA, proteins). In the method of the present invention, oligonucleotides, either modified or unmodified, which hybridize to a selected region of influenza virus RNA ((−)vRNA; (+)mRNA and/or (+)cRNA) are introduced into cells under conditions appropriate for hybridization of the oligonucleotides to the selected region of virus RNA. The oligonucleotides hybridize with the influenza virus RNA, interfering with its ability to serve as a template for synthesis of encoded products and, thus, resulting in inhibition of influenza virus replication and/or gene expression.

The present invention also relates to oligonucleotides which have antiviral activity against influenza virus as a result of their ability to hybridize to a selected region of influenza virus RNA and inhibit its ability to serve as a template for synthesis of encoded products. Modified oligonucleotides of the present invention can include one or more modifications of the nucleic acid bases, sugar moieties, internucleoside phosphate linkages, or a combination of modifications at these sites. The internucleoside phosphate linkages can be phosphorothioate, phosphoramidate; methylphosphonate, phosphorodithioate and combinations of such or similar linkages (to produce mixed backbone modified oligo- nucleotides). The modifications can be internal or at the end(s) of the oligonucleotide molecule and can include additions to the molecule of the internucleoside phosphate linkages, such as cholesteryl, diamine compounds with varying numbers of carbon residues between the amino groups and terminal ribose, deoxyriboase and phosphate modifications which cleave, or crosslink to the opposite chains or to associated enzymes or other proteins which bind to the viral genome. For example, the replicase is adjacent to certain antisense oligomers synthesized. Electrophilic groups such as a ribose-dialdelyde could covalently link with an epsilon amino group of the lysyl residue of such a protein. A nucleophilic group such as n-ethylonaleimide tethered to an oligomer could covalently attach to the triphosphate cap of an mRNA or to another electrophilic site. The present invention further relates to compositions having antiviral activity against influenza virus, which include the oligonucleotides of the present invention, and to a method of administering the oligonucleotides or compositions containing modified oligodeoxynucleotides to an individual for the purpose of inhibiting influenza virus replication.

In a specific embodiment of the method of the present invention, modified oligodeoxynucleotides which have antiviral activity against influenza virus are introduced into cells, in which they hybridize to a selected region of influenza virus RNA (either the (−) or the (+) strand of the influenza virus genome), inhibiting replication or expression of encoded products; as a result, influenza virus replication is inhibited. The modified oligodeoxynucleotides used in the present method are complementary to a region of influenza virus RNA which is essential for influenza virus replication and/or gene expression. The modified oligodeoxynucleotides can include modifications of the nucleic acid bases, the internucleoside phosphates, the sugar moiety, or a combination of modifications at these sites. The modifications can be internal or at the end(s) of the oligonucleotide molecule.

The modified oligonucleotides of the present invention are sufficiently complementary to regions of the influenza virus genome that they hybridize to those regions, rendering them unavailable to serve as a template for production of another genome strand. As a result, influenza virus replication is inhibited. The modified oligodeoxynucleotides hybridize to include regions of influenza RNA which include conserved targets, such as the 13 nucleotides common to the 3'-ends of the influenza virus genome strands; the conserved nucleotide region at the 5'-terminus of the influenza virus RNA; some or all of the sequence encoding the PB1 polymerase (particularly the Asp-Asp motif of its catalytic site); the catalytic sites of the polymerase related proteins PB2 and PA; the catalytic site of the neuraminidase protein; and invariant segments of the HE, NP, M and NS proteins. According to the present method, the modified oligonucleotides enter cells, in which they hybridize to a selected region of viral RNA, which can be either the (−) or the (+) strand of the viral genome.

The modified oligonucleotides of the present invention can be administered to an individual to provide protection against influenza virus. The modified oligonucleotides are administered to an individual, generally as a component of a composition which also includes a physiologically acceptable carrier. After administration, the oligonucleotides enter cells, hybridize to viral RNA and inhibit its ability to serve as a template for synthesis of encoded products. As a result, replication of the influenza virus is inhibited and the effects of the influenza virus on the individual are less than they would have been if the modified oligonucleotides had not been administered. The protection established as a result produces either resistance to infection by influenza virus (with the result that infection by the virus does not occur) or a reduced level of infection in an individual (with the result that infection occurs, but to a lesser extent than would have occurred if the modified oligonucleotides had not been administered).

Use of such modified oligonucleotides has at least two important advantages. First, the antiviral effects observed are very specific, in the following sense: A specific sequence of 20 nucleotides would not be expected to occur at random more often than once in $10^{12}$. There are approximately $4 \times 10^9$ nucleotides in the human genome and, thus, the specificity of, for example, a 20-nucleotide sequence chosen from the influenza virus genome is predicted to be great. Second, the cellular toxicity of the oligonucleotides is low.

BRIEF DESCRIPTION OF THE DRAWINGS

FIG. 2 is a graphic representation of the effect of unmodified ODNs (O-ODN) and phosphorothioate derivatives of ODN (S-ODN) on influenza virus A replication.

FIG. 3 is a graphic representation of inhibition of influenza virus A replication by S-ODN.

DETAILED DESCRIPTION OF THE INVENTION

Figure 1:
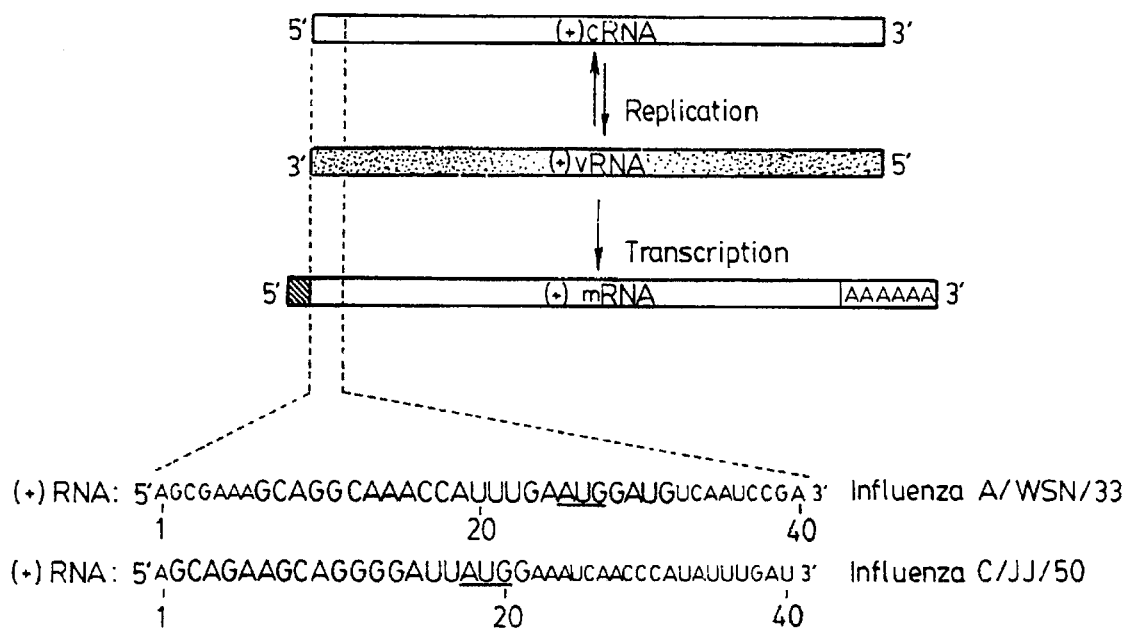
FIG. 1 is a schematic representation of the three different types of RNA present in cells infected by influenza virus and partial RNA sequences of two influenza viruses. The three bars at the top of FIG. 1 represent, respectively, complementary RNA (cRNA); viral RNA (vRNA); and mRNA. The host cell-derived 5' portion (hatched) and the polyadenylated 3' portion of the mRNA are indicated. The two sequences represented in the lower half of the figure are, respectively, part of the RNA sequence of the PB1 gene of influenza A/WSN/33 virus and part of the RNA sequence of influenza C/JJ/50 virus, both in the (+) sense orientation. The regions corresponding to the oligonucleotides tested are printed in boldface; initiation codons are underlined.

The present invention relates to a method of inhibiting (reducing or preventing) influenza virus replication in cells through use of oligonucleotides which hybridize to a selected region of influenza virus RNA and inhibit (reduce or eliminate) its ability to serve as a template for synthesis of encoded products, resulting in total or partial inhibition of influenza virus replication and/or gene expression. The present invention further relates to oligonucleotides which have antiviral activity against (i.e., reduce or prevent replication of) influenza virus as a result of their ability to hybridize to a selected region of the viral genome necessary for viral replication and inhibit its ability to serve as a template for synthesis of encoded products (RNA, DNA, proteins). The oligonucleotides of the present invention can be modified or unmodified and can be oligodeoxynucleotides or oligoribonucleotides.

The present invention also relates to compositions which include oligonucleotides with antiviral activity against influenza virus; such compositions are administered, according to the method of the present invention, to an individual for the purpose of reducing the effects of the influenza virus. The oligonucleotides can be administered to an individual prior to infection with influenza virus or after infection has occurred.

As described herein, it has been shown that modified ODNs (e.g., phosphorothioate derivatives, represented herein as S-ODNs) complementary to selected regions of influenza virus RNA inhibit replication of influenza A virus and influenza C virus. At the concentrations used, unmodified ODNs (represented herein as O-ODNs) complementary to the selected regions of influenza virus RNA did not inhibit influenza virus replication. At higher concentrations, however, unmodified oligodeoxynucleotides might be effective in inhibiting influenza virus replication; their effectiveness can be assessed using methods described herein.

The following is a description of inhibition of influenza A virus and influenza C virus by the method of the present invention. Although the following describes use of the present method and modified oligodeoxynucleotides which hybridize with selected regions of these particular influenza viruses, the present method is also useful for inhibiting other strains of influenza virus (e.g., influenza B virus). The present method can also be carried out using modified oligonucleotides which hybridize to regions of influenza virus RNA other than those specifically described. Regions of influenza virus RNA necessary for viral replication, particularly those which are conserved among different virus strains, are appropriate targets for modified oligonucleotides of the present invention. These regions of influenza virus RNA include the 13 nucleotides common to the 3'-ends of the influenza virus genome strands; the conserved nucleotide region at the 5'-terminus of the influenza virus RNA; some or all of the sequence encoding the PB1 polymerase (particularly the Asp-Asp motif of its catalytic site); the catalytic sites of the polymerase related proteins PB2 and PA; the catalytic site of the neuraminidase protein and the invariant segments of the HE, NP, M and NS proteins.

Any or all of the three forms of influenza virus RNA (viral RNA, mRNA and complementary RNA) are potential targets for the oligonucleotides of the present invention. The three forms are represented in FIG. 1. In the case of a negative-stranded viral genome, such as is present in influenza virus, the viral RNA, designated (−)vRNA, serves as a template for synthesis by the viral replicase of a (+)-strand RNA, which can be converted into an mRNA. An oligomer complementary to the mRNA can then be called an antisense RNA. An oligomer which is complementary to the viral ((−)vRNA) may be regarded as antisense to the viral RNA and, as represented in FIG. 1, is designated (+)cRNA. In the method of the present invention, oligonucleotides capable of hybridizing to any of these three types of influenza virus RNA can be used, individually or in combination with either or both of the other type of oligonucleotides. For example, modified oligonucleotides capable of hybridizing to influenza virus mRNA can be introduced into cells, alone or in combination with modified oligonucleotides capable of hybridizing to influenza virus vRNA and/or with modified oligonucleotides capable of hybridizing to influenza virus cRNA. The length of the oligonucleotides used in the present method will vary, depending, for example, on the selected region of influenza virus RNA to which they are to hybridize. Typically, they are at least 6 nucleotides long; in a preferred embodiment, they are 17–25 nucleotides long.

Within a selected influenza virus RNA sequence, a region or regions essential for viral replication is/are selected. Modified oligonucleotides capable of hybridizing to that region (or regions) are produced and introduced into cells under conditions appropriate for hybridization of complementary nucleotide sequences. Under such conditions, hybridization of influenza virus RNA with the introduced complementary modified oligonucleotides occurs; this hybridization is very specific because of the selection of sequences present in the virus RNA, but unlikely to be present in human cellular DNA. The nucleotide sequences of modified oligonucleotides which have antiviral activity against influenza virus need not be wholly (100%) complementary to a region of influenza virus RNA to be useful in the present method. It is only necessary that the nucleotide sequence of a modified oligonucleotide be sufficiently complementary to a selected region of influenza virus RNA that it hybridize to the region and remain hybridized under the conditions used.

As described and exemplified herein, phosphorothioate derivatives of oligodeoxynucleotides (phosphorothioate oligodeoxynucleotides or S-ODNs) which hybridize to a region of influenza virus RNA have been shown to be effective in inhibiting virus replication. The PB1 RNA of influenza A/WSN 33 was initially chosen as the target for inhibition by antisense oligonucleotides. The PB1 RNA of influenza A/WSN/33 virus was chosen as a target for the following reasons: (i) The influenza virus protein PB1 is part of the polymerase complex that is required for transcription and replication of viral RNA. The PB1 protein is the most highly conserved protein of this complex and is the only one in which the Asp-Asp motif, which is found in many RNA polymerases, is conserved among influenza A, B, and C viruses. Taken together, this suggests an essential function of the PB1 gene for virus growth and any interference with its expression is likely to result in decreased virus titers. (iii) Influenza virus polymerase mRNAs are expressed at relatively low levels in infected cells, as compared to other viral mRNAs. Thus, a lower intracellular concentration of S-ODN should be required to block gene expression. (iii) The ends of the PB1 gene were chosen as targets because a high degree of conservation was observed at the 3' and 5' ends among the genomic segments of influenza viruses. Therefore, if part of the ODN sequence is conserved among different RNA segments, this may result in the inhibition not only of the PB1 gene, but of several other genes as well. (The results of a computer analysis of ODN target sites in the influenza C virus genome are discussed in Example 1.) In particular, S-ODNs which were complementary to the polymerase PB1 genes of either influenza A/WSN/33 virus or of influenza C/JJ/50 virus inhibited replication, respectively, of influenza A virus and influenza C virus. At the concentrations tested, unmodified oligodeoxynucleotides of the same sequence (i.e., corresponding to the polymerase PB1 genes of either influenza virus type) failed to inhibit replication of either virus. Higher concentrations were not tested, and it is likely that at a higher concentration they might have been inhibitory, as suggested by results of testing of unmodified and modified oligomers against HIV.

Demonstration of the effects of S-ODNs is described in Examples 2 and 3. Briefly, the effects were shown as follows: Because all three forms of influenza virus or virus-specific RNA are possible targets for antisense ODNs, unmodified (O-ODNs) and modified (S-ODNs) either complementary to or identical to viral sequences in the positive and the negative orientation were synthesized, using known techniques (see Example 1), and tested. The sequences of ODNs synthesized and tested are presented in the Table; see Example 1 for further description of these ODNs. Each of the sequences used was 20 nucleotides in length. The regions of the influenza virus genome complementary to or identical with the ODNs are printed in boldface in FIG. 1 and the initiation codons are underlined. In addition to ODNs targeted against the polymerase PB1 RNA of influenza A and C, ODNs containing mismatches relative to specific influenza virus sequences were produced and tested. (See Example 1 for description of the mismatches produced).

Testing of the antiviral effect against influenza A virus of the O-ODNs and the S-ODNs was carried out as described in Example 2. Madin-Darby canine kidney (MDCK) cells were infected with influenza virus prior to infection and again after infection, as described in Example 2. Testing of the antiviral effect of O-ODNs S-ODNs against influenza C virus was carried out in a similar manner, as described in Example 3.

Figure 5:
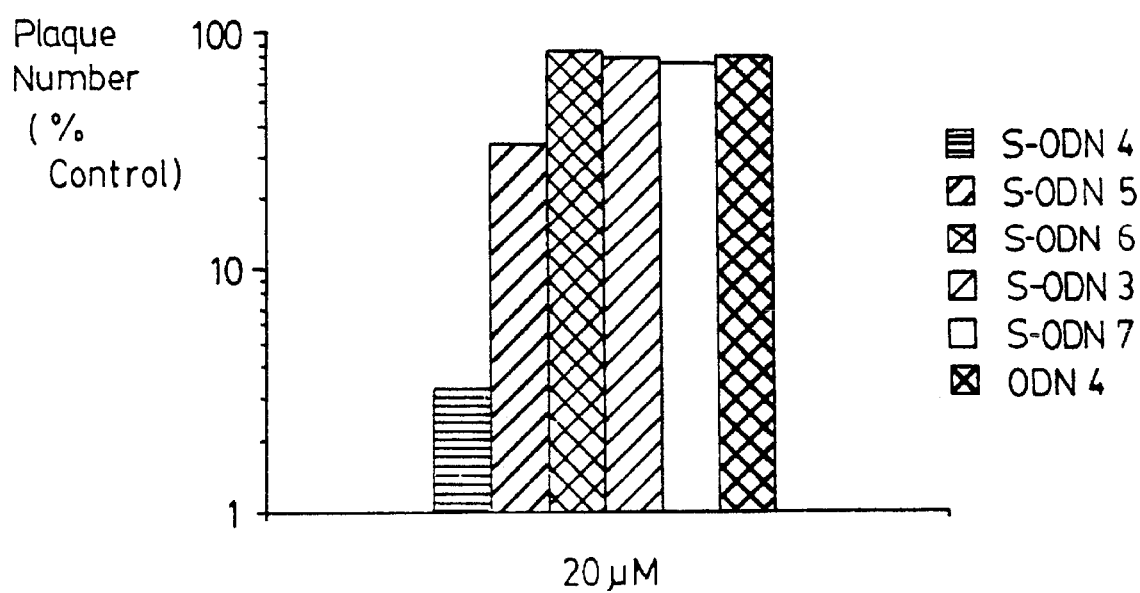
FIG. 5 is a graphic representation of sequence-specific inhibition of influenza C virus replication by S-ODN 4.

At the concentrations used, unmodified ODNs were not found to be active against either influenza A virus (FIG. 2A) or influenza C virus (FIG. 5). Based on data from assessment of the effects of ODN's on HIV, it appears that the unmodified O-ODNs are ineffective because they are rapidly degraded extracellularly and/or intracellularly. Unmodified ODNs complementary to influenza virus RNA can be introduced into cells at higher concentrations than used herein and tested for their ability to inhibit influenza virus. It is reasonable to expect that higher concentrations will inhibit the virus.

Figure 2A:
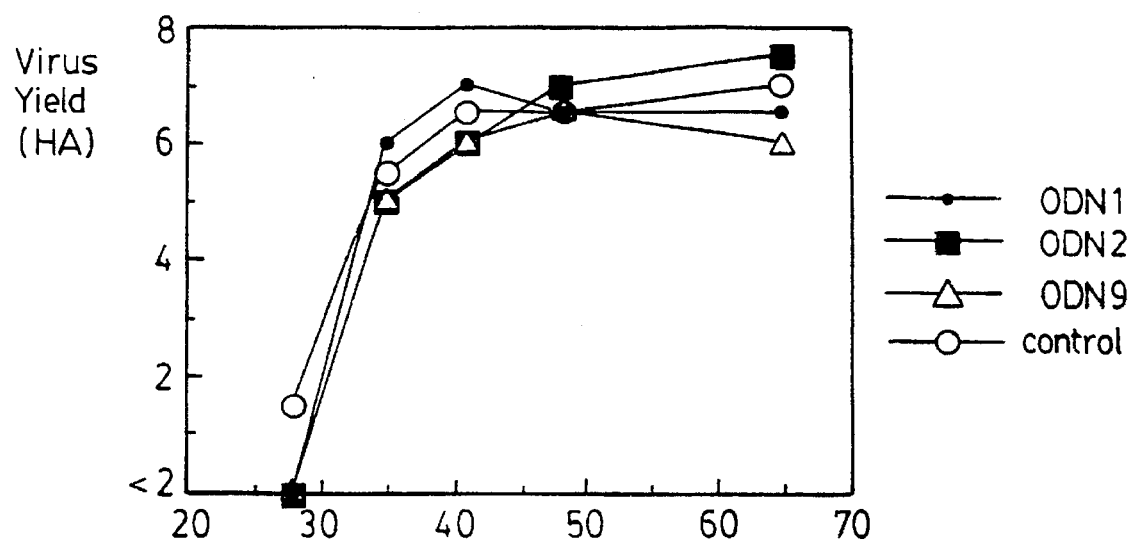
FIG. 2A shows the effects of O-ODN on influenza virus A replication.
Figure 2B:
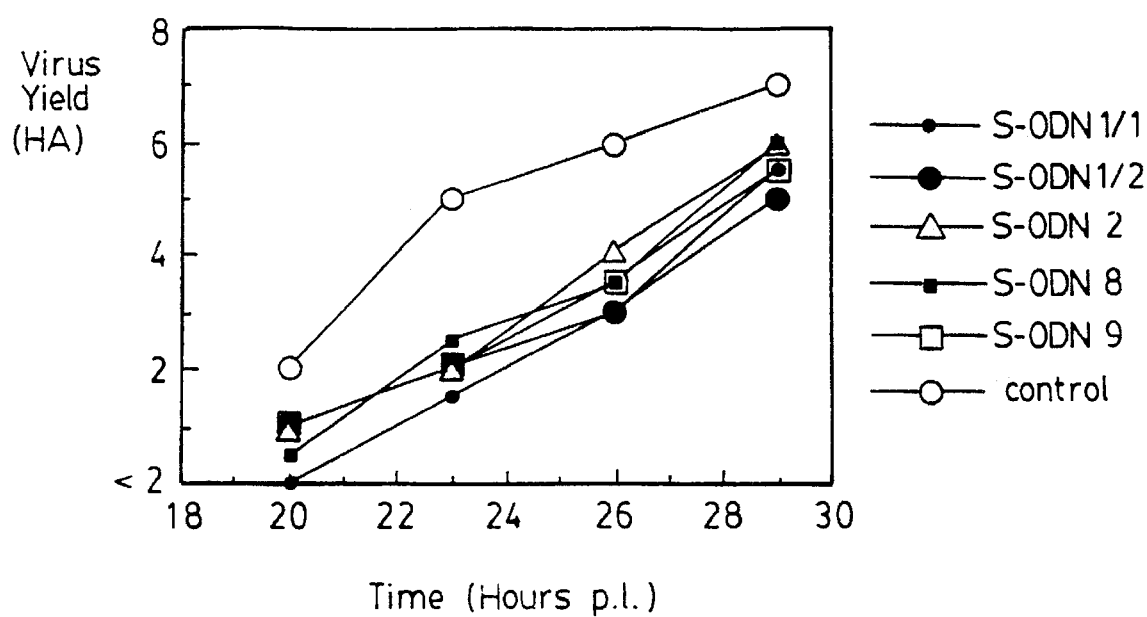
FIG. 2B shows the effects of S-ODN on influenza virus A replication.
Figure 3A:
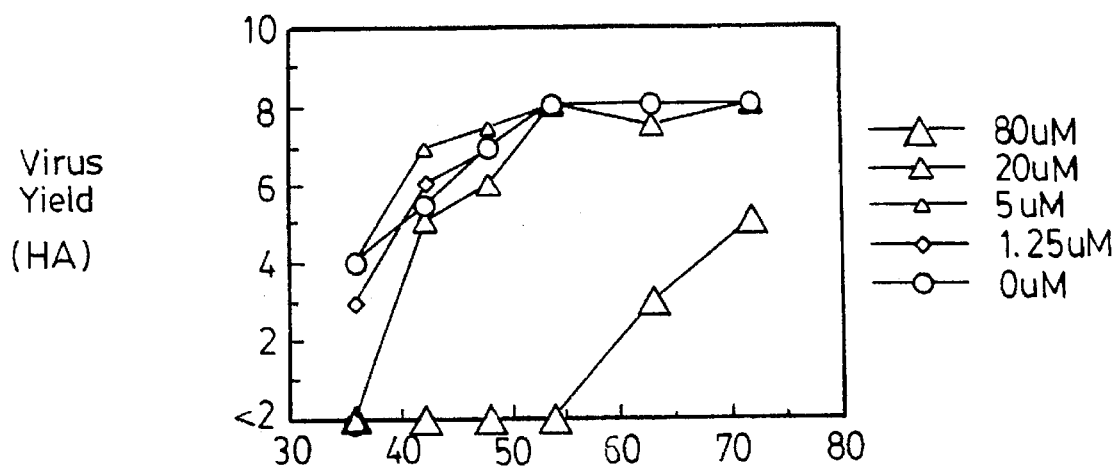
FIG. 3A shows the effects of S-ODN added 30 minutes prior to infection and continuously present throughout assessment of the effect.
Figure 3B:
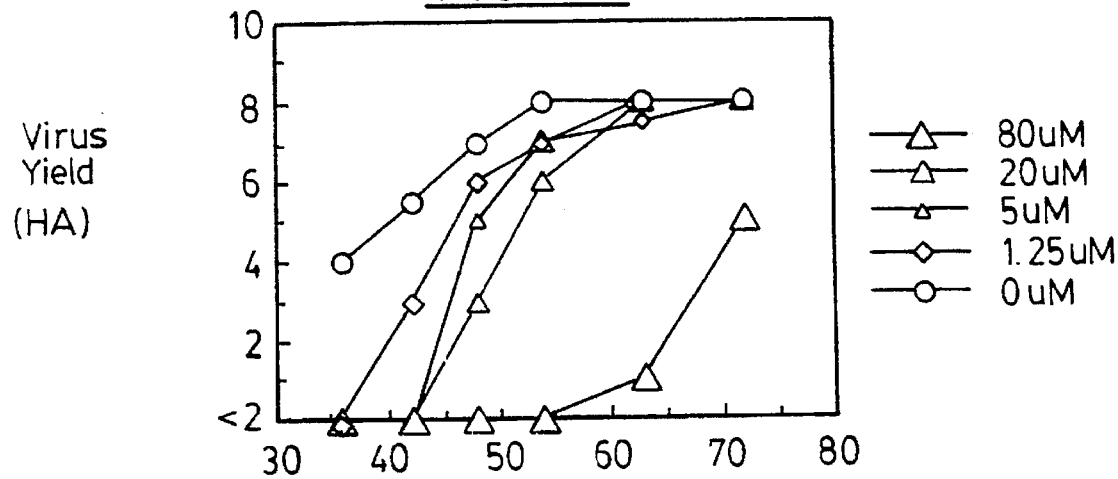
FIG. 3B shows the effects of S-ODN added 24 hours prior to infection and continuously present throughout assessment of the effect; virus yield was determined by testing hemagglutinin (HA) titers.
Figure 3C:
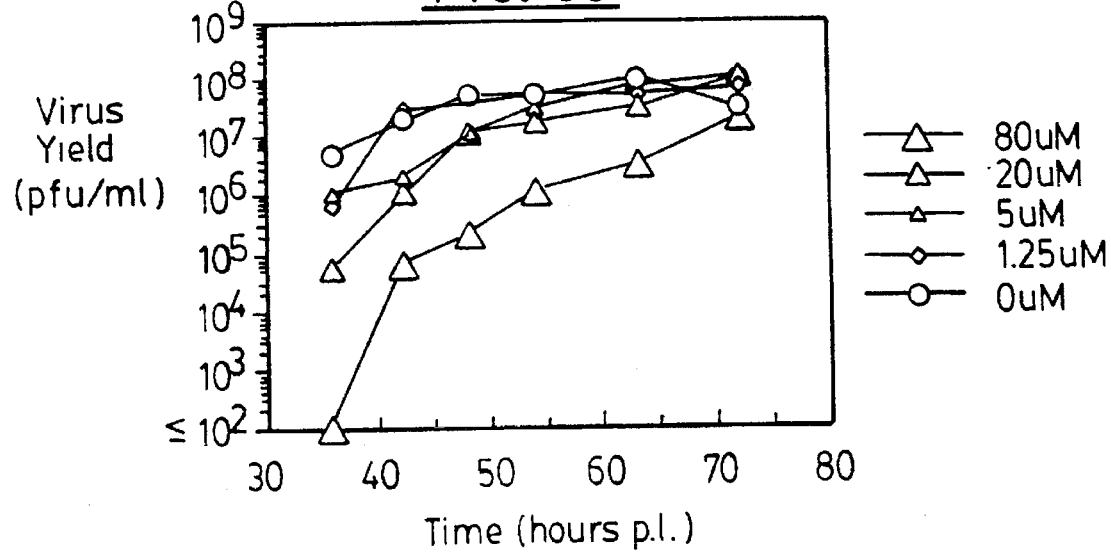
FIG. 3C shows the effects of S-ODN added as described for FIG. 3B; virus yield was determined by titration of infectious virus on MDCK cells.
Figure 6:
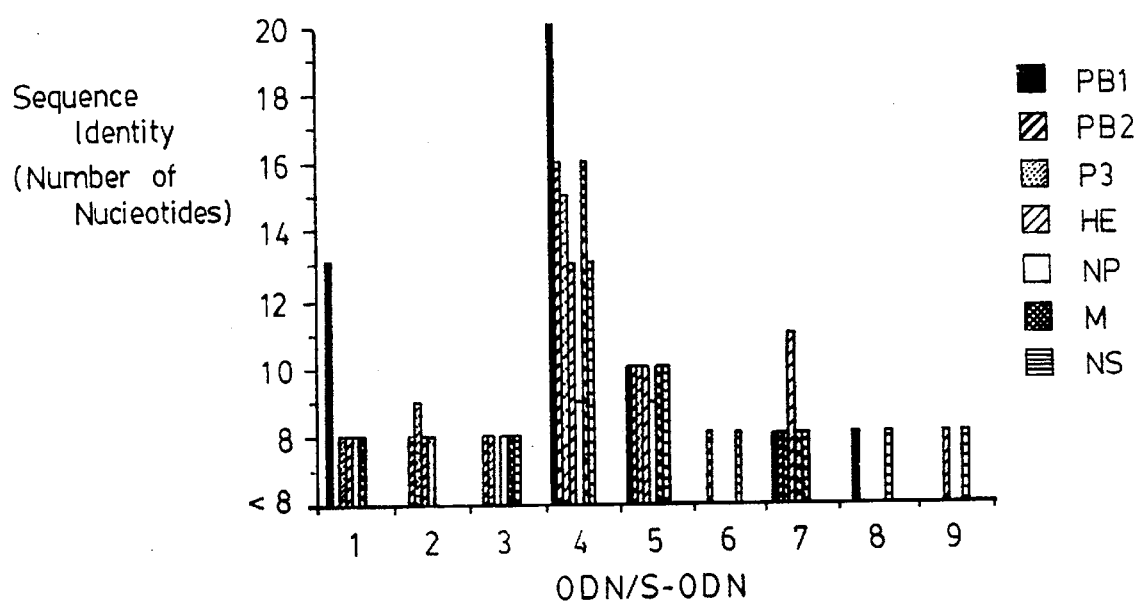
FIG. 6 shows the results of computer sequence analysis of ODNs 1–9.

Phosphorothioate derivatives showed consistent inhibitory antiviral activity in multicycle and even single-cycle replication experiments using influenza A virus (FIGS. 2B and 3). The effect was present with mismatched oligomers and most likely not the result of cytotoxic effect of the compounds. This view is supported by several lines of evidence. First, MDCK cell monolayers were found to be intact throughout the experiment in uninfected control cells treated with 80 0μM S-ODN compound. Second, S-ODNs delayed influenza A virus replication, rather than completely abolishing it (FIG. 3), which indicates that cells are able to support viral replication as late as 4 days after treatment with S-ODN. Third, these compounds were purified by the same method used for O-ODNs, which showed no antiviral activity. Therefore, it is unlikely that the observed effect is due to impurities in the preparation. However, this effect could not be correlated with a particular sequence although as shown in FIG. 6, at least 8 out of 20 contiguous nucleotides hybridize for all sequences tested, as determined by computer analysis. Furthermore, effects of mismatched S-ODNs on viral replication have also been found in the case of HIV. S-ODNs are also known to interact with reverse transcriptase and presumably with other enzymes and proteins.

Figure 4:
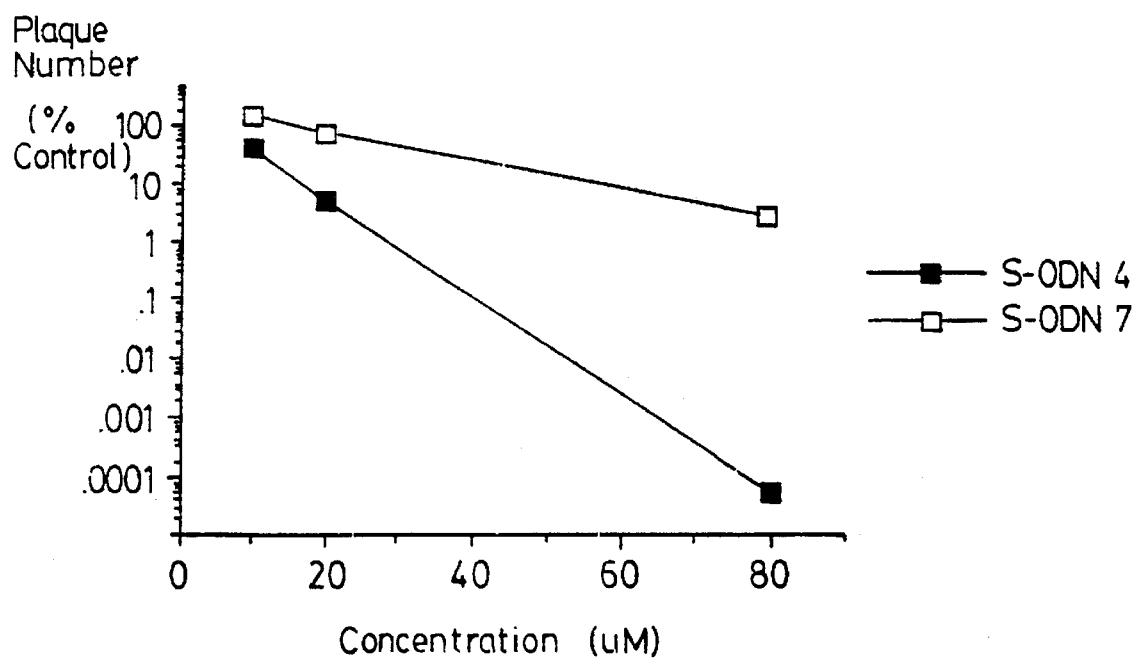
FIG. 4 is a graphic representation of the dose-dependent inhibition of influenza C virus by S-ODN.

Influenza C virus replication could be inhibited in a sequence-specific manner by using S-ODN 4. If present at 20 μM concentration in the medium, this compound was at least 10-fold more active than any of the other sequences tested (FIG. 5). The same sequence had no effect on influenza A virus replication using the same assay system (data not shown). At higher concentrations, an even more dramatic reduction of influenza virus growth was observed (FIG. 4). The complementary sequence, S-ODN 3, was found to be inactive (FIG. 5). Computer analysis was performed to examine the degree of sequence identity between the ODN sequences tested and the influenza C virus genome. It was found that six of seven viral RNA segments are complementary to at least 13 nucleotides in ODN 4 (FIG. 6). Introduction of a single mismatch in S-ODN 5 reduces the degree of sequence complementarity to 10 nucleotides, but six RNA segments still remain at potential targets. This may explain the remaining antiviral activity of this compound at a 20 μM concentration (FIG. 5). No other control, including the triple mismatched sequence of S-ODN 6, showed antiviral activity (FIG. 5) and none was complementary to more than eight contiguous nucleotides of the influenza C virus genome (FIG. 6). It has recently been found that in the case of O-ODNs, one or two mismatches between oligomer and RNA may result in loss of RNase H sensitivity of that complex. Taken together, it appears that for an S-ODN to have an anti-influenza C virus effect, it is critical that it have more than 10 contiguous nucleotides complementary to the (−)-strand viral RNA at this target site variable. The effect of hybridization mismatches on viral inhibition is variable and may depend on second structure and other features of the viral genome.

S-ODN 4 is complementary to the influenza C virus (−)-strand viral RNA at positions 2–21, while S-ODN 2 is complementary to the influenza A virus (−)-strand viral RNA at positions 8–27 (FIG. 1). Therefore, a S-ODN complementary to the influenza A virus (−)-strand viral RNA at positions 2–21 (5'-GCGAAAGCAGGCAAACCATT-3') was synthesized and tested for antiviral influenza virus activity. Again, this compound was not found to be more active than mismatched control S-ODNs. Although this difference between influenza A and C viruses is puzzling, the very different replication rates of these viruses should be taken into consideration. A slowly replicating virus such as influenza C virus may be a much better target for antisense ODN inhibition than a fast-growing virus such as influenza A.

It is known that the 3'- and 5'-termini of the influenza virus types form a hybridizing complementary panhandle. At the panhandle region is the polymerase complex, and a segment of host mRNA which serves as a primer for the polymerase. The region selected as described herein for hybridization inhibition by ODNs may therefore, be hindered to varying degrees for the above reasons, and may explain the difference between the inhibition of influenza A and C strains.

Thus, it has been demonstrated that influenza virus replication can be inhibited in cells through the activity of modified oligodeoxynucleotides complementary to a selected region of viral RNA. The modified oligodeoxynucleotides described are phosphorothioate derivatives. However, other modifications, such as internucleoside phosphoramidates, or methyl phosphorates, can be also be introduced. The resulting modified oligonucleotides can be tested, using, for example, the method described in Examples 2 and 3, for their antiviral activity against influenza virus. Two assay methods are described in Examples 2 and 3: (1) hemagglutination assay, which measures the total number of influenza virus particles (i.e., both) infectious and noninfectious particles; and (2) plaque titration, which detects infectious influenza virus particles only.

Modifications of the oligonucleotides can be at some or all of the internucleoside linkages, as well as at either or both ends of the oligonucleotide. Further, modified nucleic acid bases and/or alterations in sugar molecules present (e.g., arabinose can replace ribose) can be introduced.

Inhibition of Influenza Virus in Humans

Using internally labelled $^{32}$p-oligmers, it has been shown that modified oligodeoxynucleotides described herein enter a variety of types of cells, (e.g., liver, kidney, spleen, muscle, brain, and white blood cells of living rabbits). Based on the information gained from inhibition of influenza virus in tissue culture, it is possible to formulate a strategy for similar inhibition of influenza virus in people.

The strategy used in treating a particular individual depends on the status of the individual and the objective of the treatment. It is possible to administer modified oligodeoxynucleotides of the present invention to an individual who shows no symptoms of infection by influenza virus, but has been exposed (e.g., to individuals during a flu "epidemic") or to an individual already infected by the virus, (e.g., as assessed by clinical symptoms). In the former case, the modified oligodeoxynucleotides are used to prevent or reduce the effects of influenza virus prophylatically, and, in the latter case, therapeutically.

In either treatment situation, however, modified oligonucleotides must be administered to individuals in a manner capable of getting the oligonucleotides initially into the blood stream and subsequently into cells. Modified oligonucleotides can be administered by intravenous injection, intravenous drip or orally (e.g., in capsule form). As a result, the oligonucleotides can have the desired effects: getting into cells to slow down or prevent viral replication and/or into as yet uninfected cells to provide protection.

The dose to be administered varies with such factors as the size and age of the patient, stage of the disease and the type of modified oligonucleotide to be given.

The present invention will now be illustrated by the following examples, which are not to be considered limiting in any way.

EXAMPLE 1

Synthesis and Purification of ODNs and Their Phosphorothioate Analogues

Oligonucleotides were synthesized on an automated synthesizer (Biosearch 8700, Milligen, Bedford, Mass.). Both O-ODNs and S-ODNs were assembled by H-phosphonate chemistry. The synthesis and purification of O-ODNs and S-ODNs were carried out by the method previously reported. Agrawal, A. et al., *Proc. Natl. Acad. Sci. USA* 86:7790–7794 (1989).

ODNs Used

All three forms of virus-specific RNA (viral RNA, mRNA and complementary RNA) are potential targets for antisense ODNs (see FIG. 1). Therefore, unmodified ODNS (O-ODNs) and phosphorothioate derivatives (S-ODNs) corresponding to viral sequences in the positive or negative orientation were synthesized and tested for antiviral activity. The sequences of the ODNs tested are presented in Table I.

influenza C virus genome that are identical with at least eight contiguous nucleotides of ODN sequences. This was done by setting the mask to "++++++++" and searching the data base with the query sequence ODN 1 –9. The data base was comprised of the influenza C virus sequences found in GenBank release 60.0 and the sequences of the C virus polymerase genes. Yamashita, M. et al., *Virology* 171:458–466 (1989). S-ODN 8 and S-ODN 9 were found to share not more than 10 contiguous nucleotides with the (−) strand viral RNA of influenza A virus. Concentrations of ODNs were determined by absorbance at 260 nm, taking into account the molar extinction coefficient of the nucleotides present in each sequence. Ausubel, F. M. et al., *Current Protocols in Molecular Biology* (Wiley, N. Y.), 1987.

EXAMPLE 2

Assessment of Antiviral Activity of O-ODNs and S-ODNs Against Influenza Virus Viruses and Cells. Influenza A/WSN/22 (ts$^+$) virus was grown in Madin-Darby canine kidney (MDCK) cells as

TABLE I

Sequences of Oligodeoxynucleotides Tested for Antiviral Activity Against Influenza Virus

| ODN/S-ODN | Sequence | | |
|---|---|---|---|
| 1 | 5'-CATTCAAATGGTTTGCCTGC-3' | (−) Sense | A/WSN/33 |
| 2 | 5'-GCAGGCAAACCATTTGAATG-3' | (+) Sense | A/WSN/33 |
| 3 | 5'-CCATAATCCCCTGCTTCTGC-3' | (−) Sense | C/JJ/50 |
| 4 | 5'-GCAGAAGCAG9GGATTATGG-3' | (+) Sense | C/JJ/50 |
| 5 | 5'-GCAGAAGCAGAGGATTATGG-3' | S-ODN 4 with 1 mismatch | |
| 6 | 5'-GCATAAGCAGAGGATCATGG-3' | S-ODN 4 with 3 mismatches | |
| 7 | 5'-GGCAAGCTTTATTGAGGCTT-3' | Mismatched | |
| 8 | 5'-ATCTTCATCATCTCAGAGAT-3' | Mismatched | |
| 9 | 5'-CGTAAGCAACAGTACTCCTA-3' | Mismatched | |

ODNs 1–2 and 3–4 are targeted against the polymerase PB1 RNA of influenza A/WSN/33 virus (Sivasubramanian, N. and D. P. Nayak, *J. Virol.* 44:321–329 (1982)) and C/JJ/50 virus (Yamashita, M. et al., *Virology* 171:458–466 (1989)), respectively. The regions of the viral genome corresponding to the ODN are printed in boldface in FIG. 1; the initiation codons are underlined. ODNs 5–9 contain different numbers of mismatches relative to specific influenza virus sequences. Specifically, ODN 5 and ODN 6 are derived from ODN 4 by introducing point mutations at the indicated positions (underlined). ODNs 7–9 represent sequences not found in the influenza virus genome.

For each sequence, up to eight different batches of oligomers were synthesized. Each batch was tested in at least two independent experiments, which yielded comparable results.

Phosphorothioate derivatives of ODN 1 (S-ODN 1) and ODN 2 (S-ODN 2) were synthesized. Two different control sequences, S-ODN 8 and S-ODN 9, were also made. S-ODN 8 and S-ODN 9 were examined by computer sequence analysis for their occurrence in the influenza A virus genome.

Computer sequence analysis. Sequence analysis was performed on a Vax 11/780 computer running under the VMS 4.6 operating system. Version 6.1 of the sequence analysis software package by the Genetics Computer Group (Madison, Wis.) was used. Deveruex, J. et al., *Nucleic Acids Res.* 12:387–395 (1984). The WORDSEARCH program, which is based on the algorithm of Wilbur and Lipman (Wilbur, W. J. and D. J. Lipman, *Proc. Natl. Acad. Sci. USA* 80:726–730 (1983), was used to identify regions in the described. Sigiura, A., K. et al., *J. Virol.* 10:639–647 (1972). Influenza C/JJ/50 virus was grown in the amniotic sac of 11 day-old embryonated chicken eggs at 35° C.

Virus Yield Assay. MDCK cells (2×10$^5$ cells per well) were seeded into 24-well dishes (Nunc) and allowed to grow overnight. The next day, cells were washed with phosphate-buffered saline (PBS) and 200 μl of minimal essential medium containing 0.2% bovine serum albumin (MEM-BA) containing the ODN was added to each well. At various times after addition of compound, 50 l of virus sample, containing 2×10$^5$ plaque-forming units (pfu) in MEM-BA, was added per well. In some experiments, only 200 pfu per well were used to allow for multicycle replication. After adsorption for 25 minutes at 37° C., cells were washed twice with PBS, and 1 ml of MEM-BA containing the ODN and trypsin (3 μg/ml) was added. Cells were incubated at either 37° C. or 33° C. and samples of medium were taken at various times after infection for hemagglutination assay and titration on MDCK cells.

Plaque Formation Assay. MDCK cells were grown in 35-mm dishes. Confluent cells were infected with serial 1:10 dilutions of virus (100 μl per dish). One hour after infection, the inoculum was aspirated and agar overlay (2.4 ml per dish) containing 3 μg of trypsin per ml and ODN at the indicated concentration was added. Cells were incubated at either 37° C. for 2.5 days (influenza A virus) or 33° C. for 4–5 days (influenza C virus).

Using the methods described above, unmodified ODNs were tested for antiviral activity using influenza A virus. O-ODN 1, O-ODN 2 and O-ODN 7 (Table and FIG. 1) were synthesized and assayed for antiviral activity. Cells were infected at a low multiplicity of infection (moi) (0.001) to allow for multicycle replication of the virus. O-ODNs were added 30 minutes prior to infection and again 24 hours after infection. The concentrations in the medium were 80, 27 and 9 µM. No antiviral activity was observed at any concentration (FIG. 2A and data not shown). Similar results were obtained for influenza C virus (see below).

Virus replication was tested under multicycle (moi 0.001) and single-cycle (moi 1) conditions. Most experiments were performed at 37° C., but for some infections a temperature of 33° C. was chosen. If the mechanism of action involves hybridization of S-ODNs to viral RNA, it was thought that this experimental condition might enhance the antiviral effect. The result of a typical experiment, performed at 33° C. and a moi of 1, is shown in FIG. 2B. All sequences tested were found to inhibit growth of influenza A virus when supplied in the phosphorothioate form. However, inhibition with mismatched oligomers was also observed. As expected, the antiviral effect was significantly stronger under multicycle replication conditions (FIG. 3A) and could be further enhanced by pretreating cells with S-ODN (FIGS. 3B and C). Under these conditions, the compounds were active at concentrations as low as 1.25 µM (FIG. 3 and data not shown).

EXAMPLE 3

Inhibition of Influenza C Virus Using S-ODN 4

Influenza C virus grows more slowly than influenza A virus and the experimentation period is longer. Therefore, a faster assay system was used for A virus to determine inhibition of influenza C virus. Briefly, S-ODNs were added to the agar overlay and plaques were counted at the end of the incubation period. In preliminary experiments, influenza A virus was assayed by this system and again inhibition with mismatched oligomers was obtained (data not shown). Sequences tested against influenza C virus included S-ODN 3 (complementary to (+)-RNA of C virus), S-ODN 4 (complementary to (−)-RNA of C virus), and S-ODN 7 (complementary to poly(A) signal of HIV-1). In initial experiments, performed at a concentration of 80 µM, complete inhibition of influenza C virus plaque formation was observed when S-ODN 4 was used, but not with S-ODN 3 or S-ODN 7. To confirm this result, S-ODN 4 was synthesized in three different batches. Each batch was tested in two independent experiments and essentially the same results were obtained. Concentration dependence was then examined. A sequence-specific antiviral effect was observed at concentrations as low as 20 µM (FIG. 4). To define further the degree of specificity, single (S-ODN 5) and triple (S-ODN 6) mismatched derivatives of S-ODN 4 (FIG. 1) were used. S-ODN 5 was significantly less active than S-ODN 4 at a concentration of 20 µM (FIG. 5). S-ODN 6, as well as various other control sequences including the complementary sequence S-ODN 3, were found to be inactive at that concentration (FIG. 5). Phosphodiester derivative O-ODN 4 was completely inactive, at any concentration tested (FIG. 5; data not shown).

EXAMPLE 4

Inhibition of Influenza A Virus by Oligodeoxynucleotides in Mice

Animals: 69 female Balb/c mice—6 weeks old
Virus: Influenza A/PR/8/34
Infection: as an aerosol, on day 0

Oligos: dissolved in sterile saline, administered on days 0, 1 and 2 (1 hour before infection, 24 and 48 hours after infection).

Mode of Administration: either 1 mg intranasally (i.n.) (under ether anesthesia) or 0.5 mg i.n. and 0.5 mg intraperitoneally (i.p.). as a control, saline was given i.n. and i.p.

Experiment 35 mice (Group A) were sacrificed on day 3 for titration of infectious virus from lungs (titres are given as Pfµ/ml of lung volume), 34 mice (Group B) were observed for survival.

Results
Group A

| Oligodeoxynucleotide Complementary to mRNA - sequence as shown for ODN1 in Table 1 | | |
| --- | --- | --- |
| i.n. | 2.1 (±1.0) × 10⁸ pfµ/ml | (n = 5) |
| i.n. & i.p. | 4 (±1.0) × 10⁸ pfµ/ml | (n = 5) |
| Oligodeoxynucleotide Complementary to vRNA - sequence as shown for ODN2 in Table 1 | | |
| i.n. | 1.3 (±0.6) × 10⁸ pfµ/ml | (n = 5) |
| i.n. & i.p. | 6.6 (±2.7) × 10⁸ pfµ/ml | (n = 5) |
| Mismatched Oligodeoxynucleotide - sequence as shown for ODN7 in Table 1 | | |
| i.n. | 2.0 (±0.8) × 10⁸ pfµ/ml | (n = 4) |
| i.n. & i.p. | 7.0 (±2.2) × 10⁸ pfµ/ml | (n = 5) |
| Control | | |
| | 2.9 (±0.2) × 10⁸ pfµ/ml | (n = 6) |

The viral titre of animals given 1 mg oligodeoxynucleotide complementary to vRNA (ODN2 in Table 1) was approximately one half that of control animals.

Group B

All mice died between day 5 and day 7.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A modified oligonucleotide having antiviral activity against influenza virus effected by hybridization with a portion of the RNA of said virus that is essential to influenza growth, wherein the modified oligonucleotide has from one to all modified internucleotide linkages selected from the group consisting of phosphorothioate, phosphorodithioate, alkylphosphonate, phosphoramidate, and combinations thereof, provided that at least one internucleoside linkage is a phosphorodithioate, alkylphosphonate, or phosphoramidate.

2. A modified oligonucleotide according to claim 1 wherein the portion of the RNA is a conserved nucleotide region within the sequence encoding the PB 1 polymerase.

3. The modified oligonucleotide according to claim 2 wherein the nucleotide sequence comprises a sequence selected from the group consisting of:

5'-CATTCAAATGGTTTGCCTGC-3',
5'-GCAGGCAAACCATTTGAATG-3',
5'-CCATAATCCCCTGCTTCTGC-3',
5'-GCAGAAGCAGGGGATTATGG-3',
5'-GCAGAAGCAGAGGATTATGG-3',
5'-GCATAAGCAGAGGATCATGG-3',

5'-GGCAAGCTTTATTGAGGCTT-3',
5'-ATCTTCATCATCTGAGAGAT-3', and
5'-CGTAAGCAACAGTAGTCCTA-3'.

4. A pharmaceutical composition comprising a modified oligonucleotide according to claim 2 and a pharmaceutically acceptable carrier.

5. A pharmaceutical composition according to claim 4, wherein the modified oligonucleotide is selected from the group consisting of
5'-CATTCAAATGGTTTGCCTGC-3',
5'-GCAGGCAAACCATTTGAATG-3',
5'-CCATAATCCCCTGCTTCTGC-3',
5'-GCAGAAGCAGGGGATTATGG-3',
5'-GCAGAAGCAGAGGATTATGG-3',
5'-GCATAAGCAGAGGATCATGG-3',
5'-GGCAAGCTTTATTGAGGCTT-3',
5'-ATCTTCATCATCTGAGAGAT-3', and
5'-CGTAAGCAACAGTAGTCCTA-3'.

* * * * *